United States Patent
Masuda

(10) Patent No.: US 12,201,409 B2
(45) Date of Patent: Jan. 21, 2025

(54) BIOLOGICAL INFORMATION MEASURING APPARATUS

(71) Applicant: LaView Corporation, Aichi (JP)

(72) Inventor: Hiroshi Masuda, Aichi (JP)

(73) Assignee: LaView Corporation, Aichi (JP)

( * ) Notice: Subject to any disclaimer, the term of this patent is extended or adjusted under 35 U.S.C. 154(b) by 0 days.

(21) Appl. No.: 18/359,474

(22) Filed: Jul. 26, 2023

(65) Prior Publication Data
US 2024/0032807 A1 Feb. 1, 2024

Related U.S. Application Data

(63) Continuation of application No. 18/028,206, filed as application No. PCT/JP2021/020721 on May 31, 2021.

(30) Foreign Application Priority Data

Sep. 25, 2020 (JP) .................................. 2020-160493

(51) Int. Cl.
A61B 5/022 (2006.01)
A61B 5/00 (2006.01)
A61B 5/021 (2006.01)

(52) U.S. Cl.
CPC .......... *A61B 5/022* (2013.01); *A61B 5/02125* (2013.01); *A61B 5/02233* (2013.01); *A61B 5/7282* (2013.01); *A61B 5/742* (2013.01)

(58) Field of Classification Search
CPC ... A61B 5/02233; A61B 5/7282; A61B 5/742; A61B 5/02125
See application file for complete search history.

(56) References Cited

U.S. PATENT DOCUMENTS 5,961,467 A * 10/1999 Shimazu ................ A61B 5/022
600/494
10,849,555 B1 * 12/2020 Sullivan ............... A61B 5/6824
(Continued)

FOREIGN PATENT DOCUMENTS

| JP | 2007-044364 A | 2/2007 |
| JP | 2010-214021 A | 9/2010 |

(Continued)

OTHER PUBLICATIONS

International Search Report and Written Opinion for International Application No. PCT/JP2021/020721, mailed Aug. 10, 2021.

*Primary Examiner* — Devin B Henson
*Assistant Examiner* — Jonathan M Haney
(74) *Attorney, Agent, or Firm* — Wolf, Greenfield & Sacks, P.C.

(57) ABSTRACT

A biological information measuring apparatus (10) includes a compression belt (20) to be wound around a part of a living body, a pressure adjusting unit (51) configured to change an internal pressure of the compression belt, a data acquiring unit (52) configured to acquire time-series data indicating a change in each of the internal pressure of the compression belt and a capacity of the compression belt in a period in which the internal pressure of the compression belt is changing, and a tonus-information calculating unit (53) configured to calculate, based on the time-series data, tonus information indicating a correspondence relation between a first indicator indicating pressure applied to a blood vessel wall (100) of the living body and a second indicator indicating a capacity on an inner side of the blood vessel wall.

4 Claims, 12 Drawing Sheets

(56) References Cited

U.S. PATENT DOCUMENTS

| | | |
|---|---|---|
| 2002/0188206 A1 | 12/2002 | Davis et al. |
| 2013/0109981 A1* | 5/2013 | Uesaka ............... A61B 5/0235 |
| | | 600/495 |
| 2015/0359437 A1 | 12/2015 | Maltz |
| 2016/0081565 A1 | 3/2016 | Kinoshita et al. |
| 2020/0138368 A1 | 5/2020 | Kiani et al. |

FOREIGN PATENT DOCUMENTS

| | | |
|---|---|---|
| JP | 2015-009044 A | 1/2015 |
| JP | 2017-148195 A | 8/2017 |

\* cited by examiner

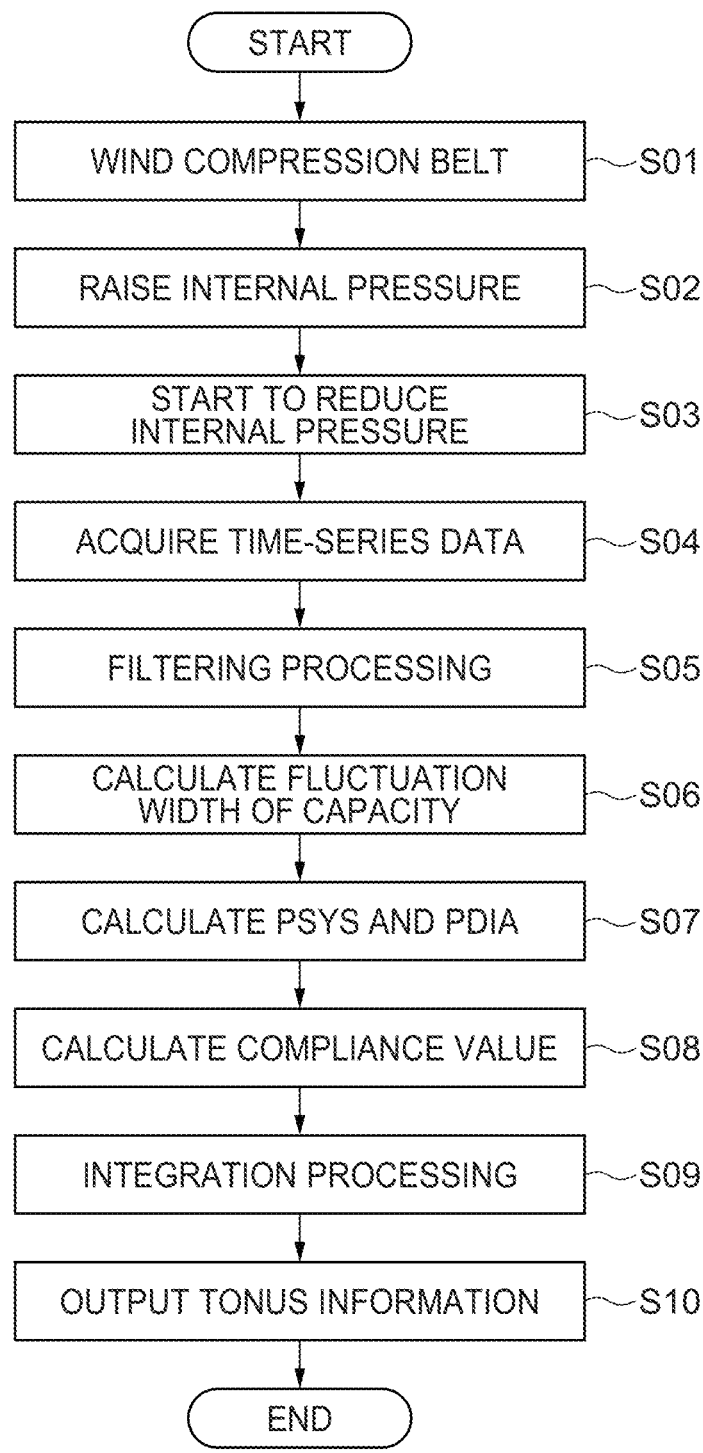

BIOLOGICAL INFORMATION MEASURING APPARATUS

CROSS REFERENCE TO RELATED APPLICATION

This application claims the benefit under 35 U.S.C. § 120 as a continuation of U.S. patent application Ser. No. 18/028,206, titled "BIOLOGICAL INFORMATION MEASURING APPARATUS," filed Mar. 23, 2023, which is a national stage filing under 35 U.S.C. § 371 of International Application Serial No. PCT/JP2021/020721, filed on May 31, 2021, which claims priority to Japanese Patent Application No. 2020-160493, filed on Sep. 25, 2020, the contents of each of these applications is incorporated herein by reference in its entirety.

TECHNICAL FIELD

The present disclosure relates to a biological information measuring apparatus.

BACKGROUND ART

In recent years, needs for easily measuring biological information have been increasing according to rising health concerns, upgrading of medical care, and the like. Examples of "biological information" include blood pressure. Patent Literature 1 below describes an apparatus that measures blood pressure using an oscillometric method.

In the oscillometric method, after a compression belt is wound around an upper arm or the like to pressurize the upper arm or the like, blood pressure is measured based on, for example, fluctuation in the capacity of the compression belt while an internal pressure of the compression belt is gradually reduced.

Since the configuration of such an apparatus is relatively simple, the apparatus has been widely adopted in ordinary homes as a biological information measuring apparatus that can be easily used.

CITATION LIST PATENT

Literature

Patent Literature 1: Japanese Patent Laid-Open No. 2015-9044

SUMMARY OF INVENTION

The present inventors have been advancing studies about a biological information measuring apparatus that can easily measure tonus information indicating a state of a blood vessel wall. The "tonus information" is biological information indicating a correspondence relation between pressure acting on the blood vessel wall in a direction of expanding the blood vessel wall and a capacity on the inner side of the blood vessel wall. As an apparatus of a related art for measuring such tonus information, there has been known a relatively complicated and large apparatus such as an apparatus that uses an ultrasonic imaging device and a strain gauge in order to measure the diameter of a blood vessel.

However, in order to easily measure the tonus information in a general home or the like, the biological measuring apparatus is preferably a simple and small biological information measuring apparatus like the manometer described in Japanese Patent Laid-Open No. 2015-9044 described above.

An object of the present disclosure is to provide a biological information measuring apparatus that can measure tonus information of a blood vessel wall, although being formed in a simple and small configuration.

A biological information measuring apparatus according to the present disclosure includes: a compression belt to be wound around a part of a living body; a pressure adjusting unit configured to change an internal pressure of the compression belt; a data acquiring unit configured to acquire time-series data indicating a change in each of the internal pressure of the compression belt and a capacity of the compression belt in a period in which the internal pressure of the compression belt is changing; and a tonus-information calculating unit configured to calculate, based on the time-series data, tonus information indicating a correspondence relation between a first indicator indicating pressure applied to a blood vessel wall of the living body and a second indicator indicating a capacity on an inner side of the blood vessel wall.

In the biological information measuring apparatus having such a configuration, the tonus-information calculating unit calculates the tonus information based on the time-series data. The time-series data is data indicating the change in each of the internal pressure of the compression belt and the capacity of the compression belt in the period in which the internal pressure of the compression belt is changing. That is, the time-series data is the same data as the data acquired by the manometer that uses the oscillometric method of the related art.

Accordingly, the biological information measuring apparatus having the configuration explained above is capable of measuring the tonus information, although being formed in a relatively simple and small configuration like the manometer or the like of the related art.

According to the present disclosure, there is provided a biological information measuring apparatus that can measure tonus information of a blood vessel wall, also being formed in a simple and small configuration.

BRIEF DESCRIPTION OF DRAWINGS

FIG. 10 is a flowchart for explaining a flow of processing executed by the biological information measuring apparatus.

DESCRIPTION OF EMBODIMENT

Figure 1:
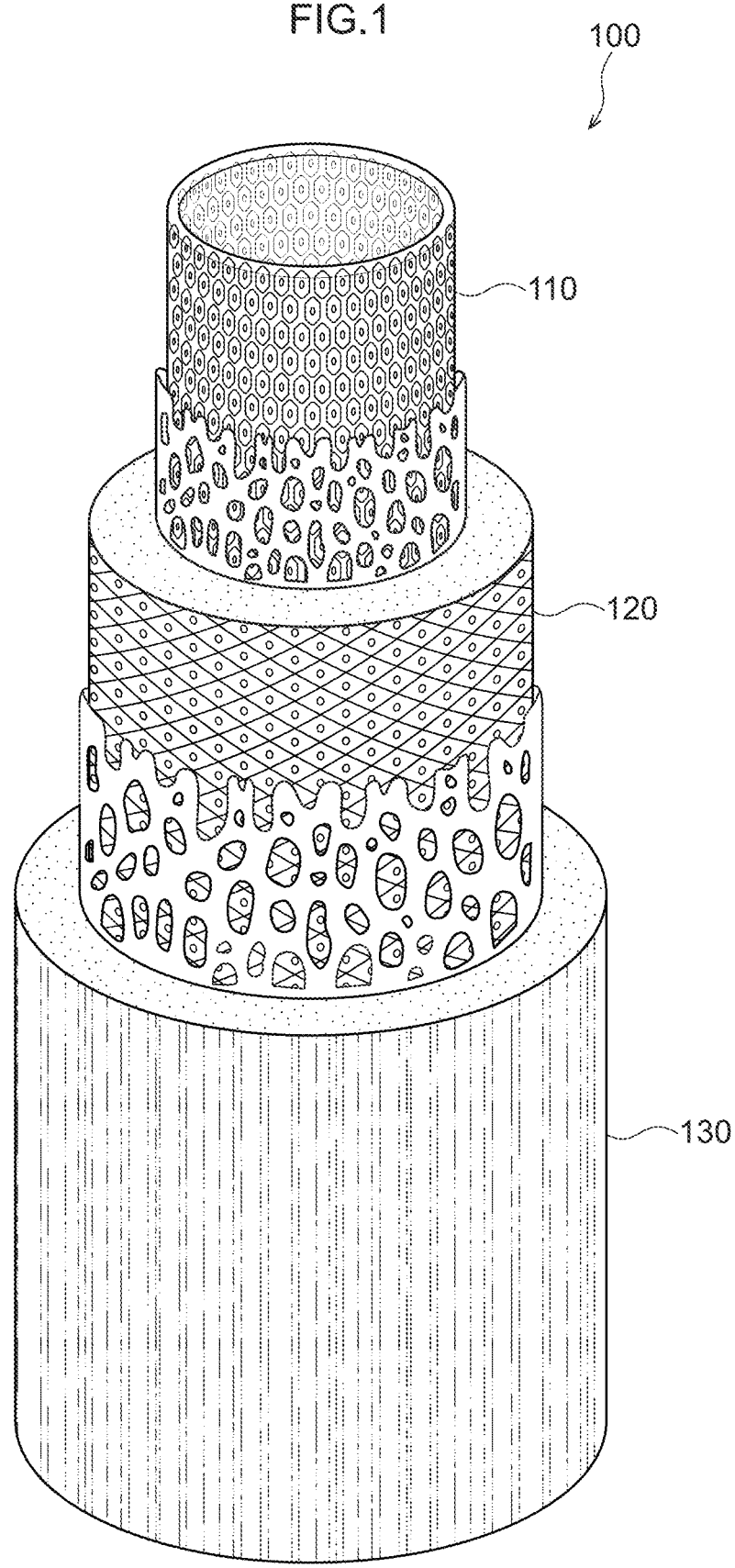
FIG. 1 is a diagram showing a configuration of a blood vessel wall.

An embodiment is explained below with reference to the accompanying drawings. In order to facilitate understanding of the explanation, the same components are denoted by the same reference numerals and signs as much as possible in the respective drawings and redundant explanation of the components is omitted.

A biological information measuring apparatus 10 according to this embodiment is configured as an apparatus for measuring tonus information of a blood vessel wall as biological information. Prior to explanation of a configuration of the biological information measuring apparatus 10, the "tonus information" to be measured is explained first.

In FIG. 1, a configuration of a blood vessel wall 100 in an artery of a human body is shown. The blood vessel wall 100 is formed in a three-layer structure including an inner membrane 110, a middle membrane 120, and an outer membrane 130. All of the membranes mainly include elastin fibers and collagen fibers.

The inner membrane 110 is a layer on the innermost side in the blood vessel wall 100. Various receptors (not shown) for detecting a state of blood are present in a vascular endothelial cell present on the innermost side in the inner membrane 110.

The middle membrane 120 is a layer present on the outer side of the inner membrane 110 in the blood vessel wall 100. An smooth muscle for adjusting an elastic state of the blood vessel wall 100 is present in the middle membrane 120. When the receptors present in the inner membrane 110 detect a blood vessel affector in blood, a tensed or relaxed state of the smooth muscle changes according to the detection of the blood vessel affector, whereby the elastic state of the blood vessel wall 100 is adjusted. The outer membrane 130 is a layer present further on the outer side of the middle membrane 120 in the blood vessel wall 100.

Figure 2:
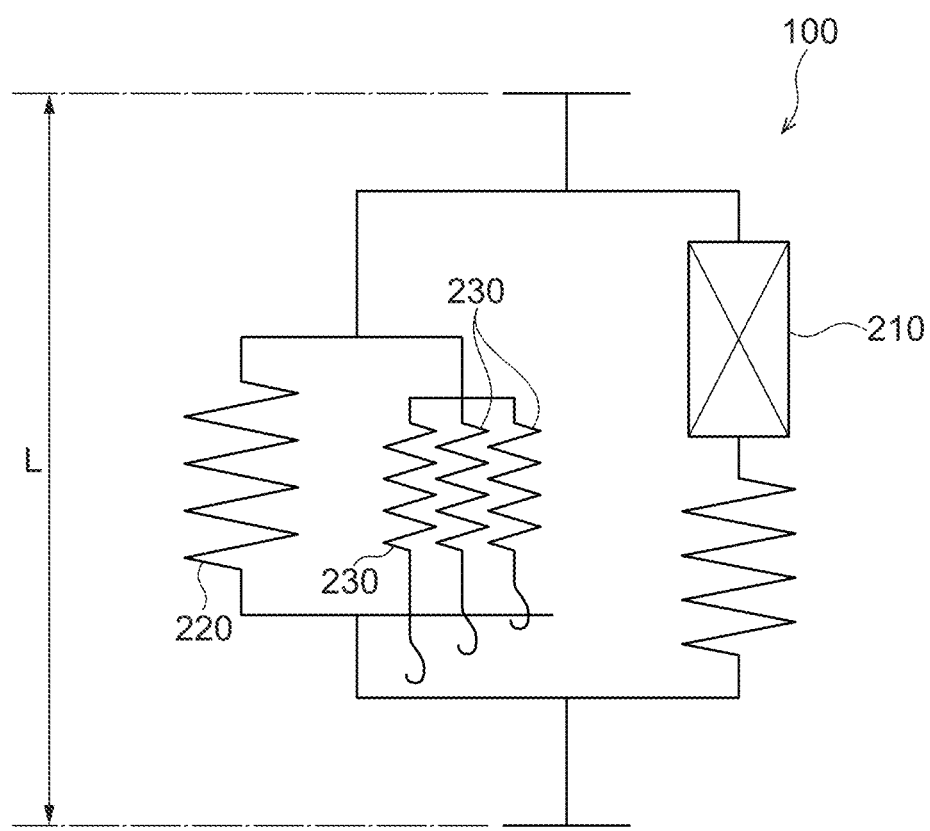
FIG. 2 is a diagram modeling and showing the blood vessel wall.

FIG. 2 is a diagram drawn by modeling the blood vessel wall 100 in order to explain an elastic property of the blood vessel wall 100. In the figure, a component denoted by a reference numeral 210 represents the smooth muscle present in the middle membrane 120. A component denoted by a reference numeral 220 represents the elastin fibers forming the respective layers of the blood vessel wall 100. A component denoted by a reference numeral 230 represents the collagen fibers forming the respective layers of the blood vessel wall 100.

A case in which the pressure on the inside of the blood vessel wall 100 rises and the blood vessel wall 100 is stretched, that is, L in FIG. 2 increases is explained. At an initial stage when the blood vessel wall 100 is started to be stretched, the elastic property of the blood vessel wall 100 is mainly affected by the smooth muscle 210 and the elastin fibers 220 and, on the other hand, is less affected by the collagen fibers 230. When the blood vessel wall 100 is further stretched, the elastic property of the blood vessel wall 100 is affected by the collagen fibers 230 as well. The influence of the collagen fibers 230 on the elastic property of the blood vessel wall 100 changes according to a degree of stretching of the blood vessel wall 100.

In this way, the elastic property of the blood vessel wall 100 is dominated by the elastin fibers 220 and the collagen fibers 230 and is adjusted by the smooth muscle 210 of the middle membrane 120. That is, the elastic property of the blood vessel wall 100 cannot be represented by only a single numerical value such as a modulus of elasticity and complicatedly changes according to pressure applied to the blood vessel wall 100 and a blood vessel affector in blood.

Figure 3:
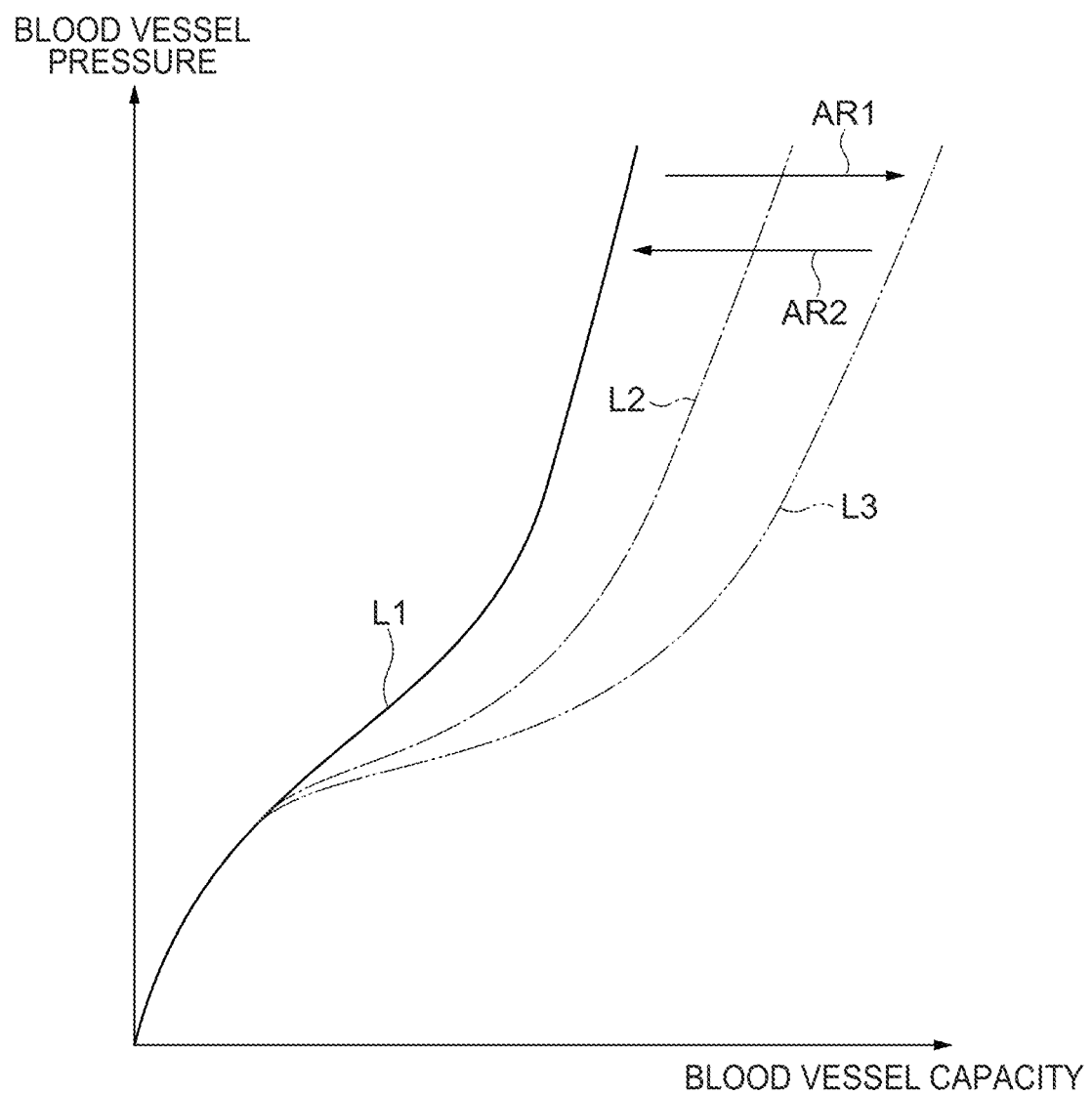
FIG. 3 is a diagram showing an example of tonus information.

In FIG. 3, an example of a correspondence relation between a blood vessel capacity (the horizontal axis) and a blood vessel pressure (the vertical axis) is shown.

The "blood vessel capacity" referred to herein means a capacity on the inner side of the blood vessel wall 100 or may be referred to as the volume of blood present on the inner side of the blood vessel wall 100 having a predetermined length.

The "blood vessel pressure" referred to herein means pressure applied to the blood vessel wall 100 in a direction in which the blood vessel wall 100 is expanded. The blood vessel pressure can be defined as, for example, (pressure applied to the blood vessel wall 100 from the outer side)–(blood pressure).

As indicated by a line L1 in FIG. 3, a graph indicating the correspondence relation between the blood vessel capacity and the blood vessel pressure is not formed in a linear shape but is formed in a unique curved shape. This is because the elastic property of the blood vessel wall 100 is affected by the smooth muscle 210, the elastin fibers 220, and the collagen fibers 230.

When a person exercises or a drug solution acting on a blood vessel is administered to a human body, the smooth muscle 210 is relaxed. Consequently, the graph indicating the correspondence relation between the blood vessel capacity and the blood vessel pressure changes in a direction of an arrow AR1 from the line L1 to a line L2 and a line L3. Conversely, when the smooth muscle 210 is tensed, the graph indicating the correspondence relation between the blood vessel capacity and the blood vessel pressure changes in a direction of an arrow AR2 from the line L3 to the line L2 and the line L1.

The "tonus information" measured by the biological information measuring apparatus 10 is information indicating the correspondence relation between the blood vessel capacity and the blood vessel pressure like, for example, respective graphs shown in FIG. 3.

Note that the vertical axis of FIG. 3 only has to be an indicator indicating pressure applied to the blood vessel wall 100 and may not be the "blood vessel pressure" itself defined as explained above. The vertical axis may be, for example, pressure including blood pressure or may be an axis on which the blood vessel pressure explained above is converted into dimensionless and represented as a parameter that changes in a range of 0 to 1. Such an indicator indicating the pressure applied to the blood vessel wall 100 is referred to as "first indicator" as well below.

Similarly, the horizontal axis of FIG. 3 only has to be an indicator indicating the capacity on the inner side of the blood vessel wall 100 and may not be the "blood vessel capacity" itself defined as explained above. For example, the horizontal axis may be an axis on which the blood vessel capacity described above is converted into dimensionless and represented as a parameter that changes in a range of 0 to 1. Such an indicator indicating the capacity on the inner side of the blood vessel wall 100 is referred to as "second indicator" as well below.

If the "tonus information" measured by the biological information measuring apparatus 10 is defined again, the "tonus information" can be considered information indicating a correspondence relation between the first indicator and the second indicator. Note that, in this embodiment, as in an example indicated by the graphs shown in FIG. 3, values of a plurality of the first indicators (the vertical axis) and a value of the second indicator (the horizontal axis) corresponding to each of the values of the first indicators are included in the "tonus information" measured by the biological information measuring apparatus 10. Instead of such an aspect, only a value of a single first indicator and a value of the second indicator corresponding to the value of the first indicator may be measured as the tonus information.

With the biological information measuring apparatus 10, the tonus information shown in FIG. 3 can be easily and quickly measured. Consequently, it is possible to determine a progression degree of arteriosclerosis based on, for example, gradients of the graphs shown in FIG. 3. It is possible to determine, based on changes of the graphs shown in FIG. 3 before and after a stimulus (for example, exercise or a drug) is applied to the human body, whether an adjusting function by the smooth muscle is soundly working.

Further, for example, when the value of the first indicator (the vertical axis) is represented as "P" and the value of the second indicator (the horizontal axis) is represented as "V", a state of the blood vessel wall 100 can be quantized using a blood vessel modulus of elasticity represented by a formula V(dP/dV). The state of the blood vessel wall 100 can also be quantized as (ΔV/V) using a change amount ΔV of the second indicator at the time when the blood vessel wall 100 is relaxed and a value (V) of the second indicator before the relaxation. In this way, if the tonus information measured by the biological information measuring apparatus 10 is used, it is possible to evaluate a health state of the blood vessel wall 100 using various indicators.

Figure 4:
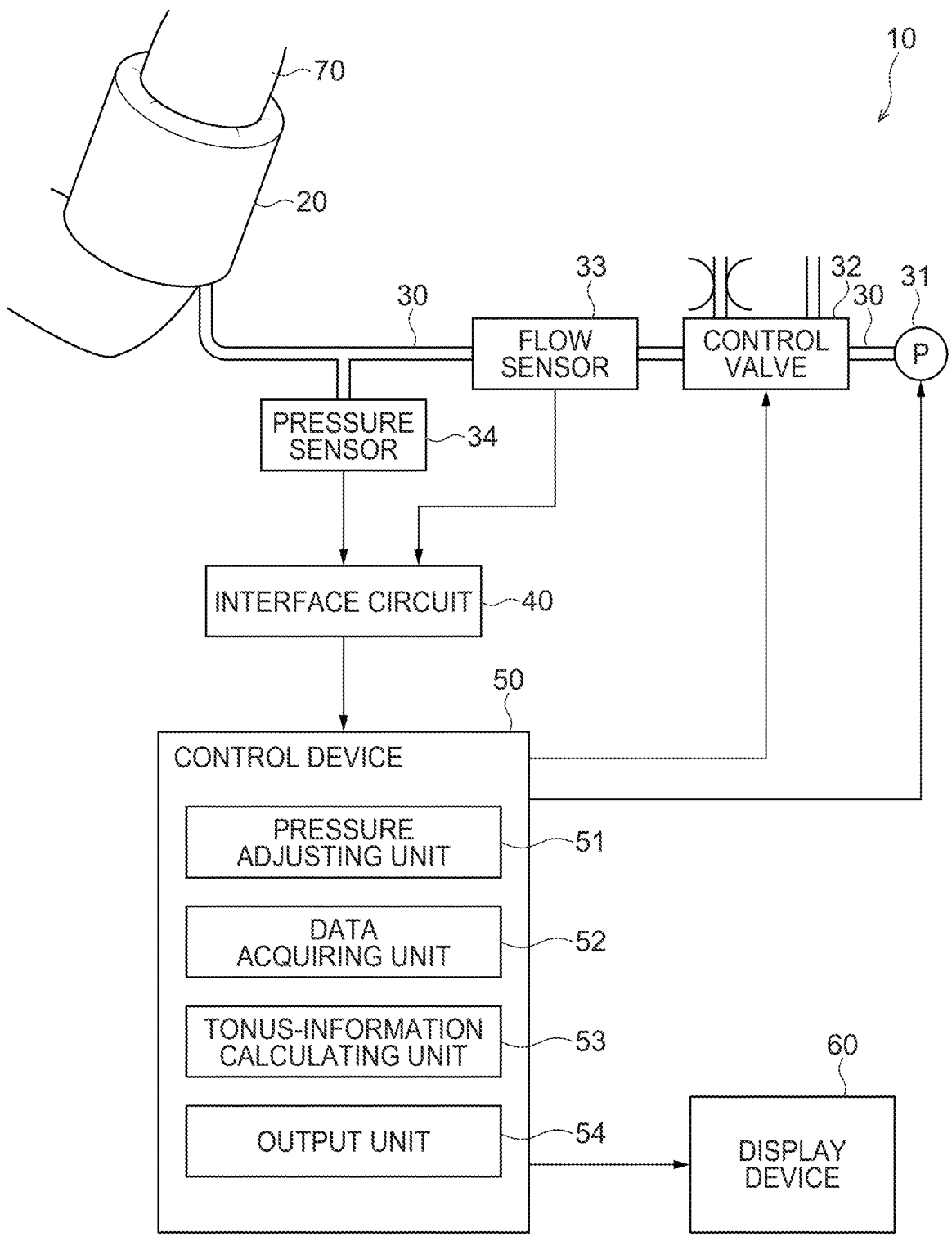
FIG. 4 is a diagram schematically showing a configuration of a biological information measuring apparatus according to an embodiment.

The configuration of the biological information measuring apparatus 10 is explained with reference to FIG. 4. As shown in FIG. 4, the biological information measuring apparatus 10 includes a compression belt 20, an air pump 31, a control valve 32, a flow sensor 33, a pressure sensor 34, an interface circuit 40, a control device 50, and a display device 60.

The compression belt 20 is a bag-like member wound around a part of a human body, which is a living body, specifically, an upper arm 70. The compression belt 20 is called "cuff" as well. When air is supplied to the inner side of the compression belt 20 and the internal pressure of the compression belt 20 rises, the upper arm 70 is pressed by the compression belt 20.

The air pump 31 is a device that blows out the air toward the compression belt 20. The air pump 31 and the compression belt 20 are connected by a pipe 30. The air blown out by the air pump 31 is supplied to the inner side of the compression belt 20 through the pipe 30, whereby the internal pressure of the compression belt 20 rises. The operation of the air pump 31 is controlled by the control device 50 explained later.

The control valve 32 is a valve for adjusting an amount of the air blown into the compression belt 20 and is provided in a position halfway in the pipe 30. The control valve 32 can also adjust an amount of the air discharged from the pipe 30 to the outside. The internal pressure of the compression belt 20 can be adjusted by such a control valve 32. The operation of the control valve 32 is controlled by the control device 50.

The flow sensor 33 is a sensor for measuring each of a flow rate of the air supplied to the compression belt 20 and a flow rate of the air discharged from the compression belt 20. The flow sensor 33 is provided in a position between the control valve 32 and the compression belt 20 in the pipe 30 and measures a flow rate of the air flowing in the position. The flow rate measured by the flow sensor 33 is transmitted to the control device 50 via the interface circuit 40 explained later. Consequently, the control device 50 can calculate and grasp capacities of the compression belt 20 at respective points in time by, for example, integrating the flow rate.

The pressure sensor 34 is a sensor for measuring the pressure of the air on the inner side of the compression belt 20, that is, the internal pressure of the compression belt 20. The pressure sensor 34 is provided in a position between the flow sensor 33 and the compression belt 20 in the pipe 30 and measures the pressure of the air in the position. The pressure measured by the pressure sensor 34 is transmitted to the control device 50 via the interface circuit 40. Consequently, the control device 50 can calculate and grasp internal pressures of the compression belt 20 at respective points in time.

The interface circuit 40 is a circuit configured as an interface for the control device 50 to receive signals from various sensors. The interface circuit 40 includes a not-shown A/D conversion circuit. An analog signal transmitted from the flow sensor 33 or the pressure sensor 34 is converted into a digital signal in the interface circuit 40 and, thereafter, input to the control device 50.

The control device 50 is a device for controlling the operation of the entire biological information measuring apparatus 10 and performing various arithmetic operations necessary for measuring the tonus information. The control device 50 is configured as a computer system including a CPU, a ROM, and a RAM. The control device 50 includes a pressure adjusting unit 51, a data acquiring unit 52, a tonus-information calculating unit 53, and an output unit 54.

The pressure adjusting unit 51 is a portion that performs processing for changing the internal pressure of the compression belt 20. The pressure adjusting unit 51 controls the operations of the air pump 31 and the control valve 32 respectively to change the internal pressure of the compression belt 20. Specifically, the pressure adjusting unit 51 performs processing for raising the internal pressure of the compression belt 20 wound around the upper arm 70 and, thereafter, gradually reducing the internal pressure.

The data acquiring unit 52 is a portion that performs processing for acquiring time-series data indicating a change in each of the internal pressure of the compression belt 20 and the capacity of the compression belt 20 in a period in which the internal pressure of the compression belt 20 is changing. The data acquiring unit 52 acquires time-series data by sampling, at a predetermined cycle, each of the internal pressure and the capacity of the compression belt 20 in a period in which the internal pressure of the compression belt 20 is gradually dropping. The internal pressure of the compression belt 20 acquired by the data acquiring unit 52 means the internal pressure of the compression belt 20 measured by the pressure sensor 34. The capacity of the compression belt 20 acquired by the data acquiring unit 52 means a capacity of the compression belt 20 calculated based on a measurement value of the flow sensor 33.

The tonus-information calculating unit 53 is a portion that performs processing for calculating, based on the time-series data explained above acquired by the data acquiring unit 52, the tonus information explained with reference to FIG. 3.

The output unit 54 is a portion that performs processing for outputting, to the outside, the tonus information calculated by the tonus-information calculating unit 53. The output unit 54 in this embodiment performs processing for transmitting the tonus information to the display device 60 explained below and causing the display device 60 to display the tonus information on a screen of the display device 60. Consequently, a user of the biological information measuring apparatus 10 becomes capable of visually checking the tonus information.

Note that the output of the tonus information by the output unit 54 is not limited to the aspect explained above. For example, the output unit 54 may output the tonus information toward a server of a medical institution. The tonus information to be output may not be output as the graphs shown in FIG. 3 but may be output as mere numerical value data.

The display device 60 is a device functioning as an interface for notifying, to the user of the biological information measuring apparatus 10, the tonus information output from the output unit 54. The display device 60 includes a not-shown screen and displays the tonus information on the screen as the graphs shown in FIG. 3. The display device 60 may be a dedicated device for displaying the tonus information but may be, for example, a portable communication terminal carried by the user.

A method of measuring the tonus information with the biological information measuring apparatus 10 is explained. First, like a general manometer, the compression belt 20 is wound around the upper arm 70. Thereafter, the pressure adjusting unit 51 raises the internal pressure of the compression belt 20 to a predetermined pressure. As the "predetermined pressure", pressure sufficient for pressing and closing the blood vessel wall 100 is est. The "closing" referred to herein means a state in which the blood vessel wall 100 in a portion around which the compression belt 20 is wound is closed by force received from the compression belt 20 and a bloodstream stops flowing.

Thereafter, the pressure adjusting unit 51 gradually reduces the internal pressure of the compression belt 20. In a period in which the internal pressure of the compression belt 20 drops, each of the internal pressure and the capacity of the compression belt 20 is sampled and acquired as the time-series data explained above by the data acquiring unit 52. This processing is continued until the internal pressure of the compression belt 20 drops to a degree not affecting the bloodstream in the blood vessel wall 100.

Figure 5:
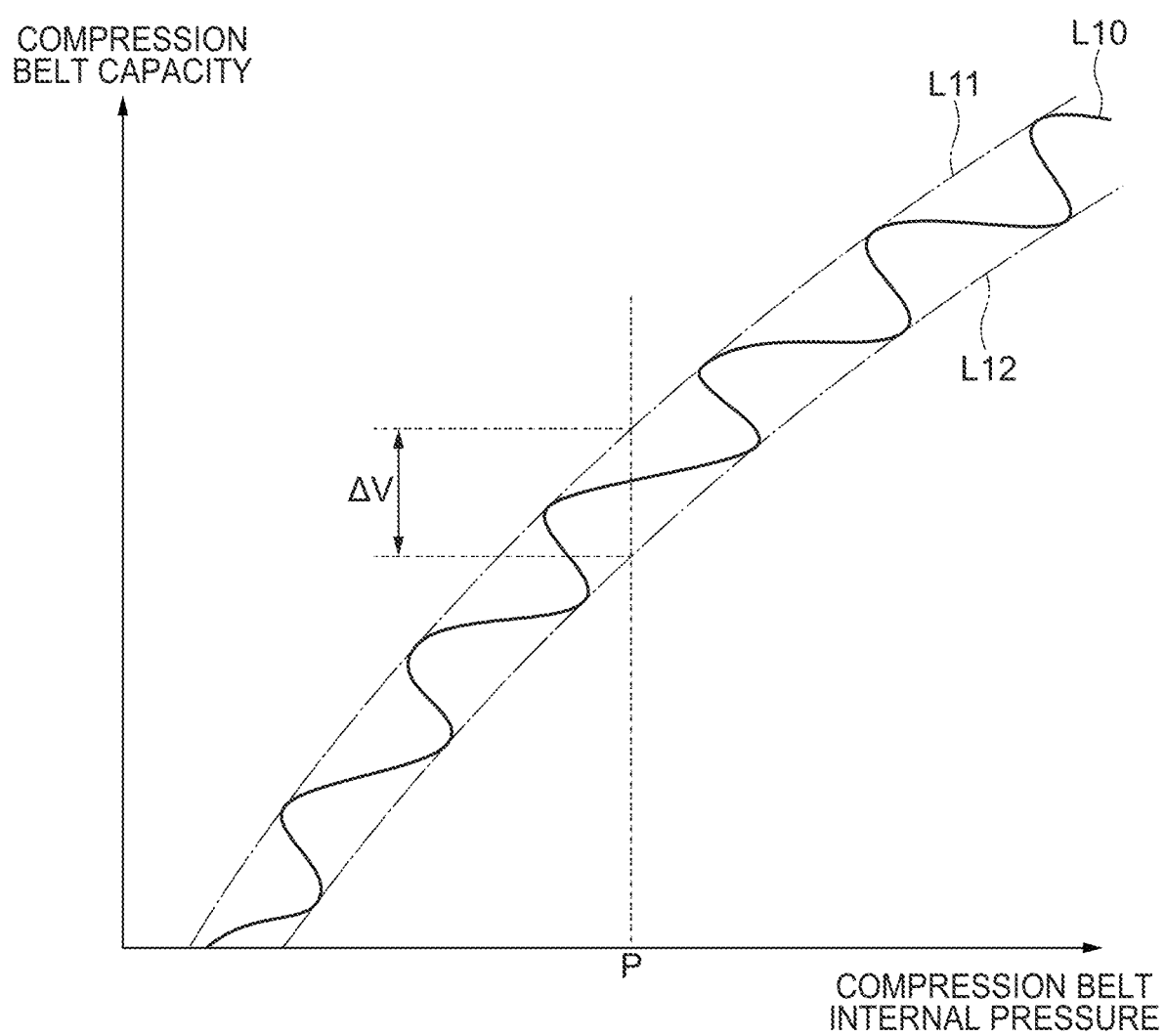
FIG. 5 is a diagram showing an example of time-series data acquired by the biological information measuring apparatus.

A line L10 in FIG. 5 is a graph indicating an example of the time-series data acquired by the data acquiring unit 52. Note that, since the time-series data is a set of a plurality of data including a combination of the internal pressure and the capacity of the compression belt 20, when the time-series data is represented as the graph shown in FIG. 5, the time-series data is actually drawn by a plurality of dots. The line L10 is obtained by drawing these plurality of dots as a continuous line.

The graph of the time-series data is a pulsating graph like the line L10 because the capacity of the compression belt 20 is affected by a beat of a heart.

When the heart enters a maximum contraction period, the blood pressure becomes the highest and the blood vessel wall 100 expands to squeeze the compression belt 20.

When the heart enters an expansion end period, the blood pressure becomes the lowest and the blood vessel wall 100 reduces and the compression belt 20 expands by the reduction.

For these reasons, even if the pressure adjusting unit 51 attempts to reduce the internal pressure of the compression belt 20, for example, at constant speed, the internal pressure drops while pulsating as indicated by the line L10.

Subsequently, the tonus-information calculating unit 53 performs processing for calculating formulas of two envelopes L11 and L12 shown in FIG. 5. The tonus-information calculating unit 53 applies filtering processing to the time-series data indicated by the line L10 to thereby extract time-series data acquired at timing when the heart enters the maximum contraction period, that is, timing at respective peaks of the pulsation and creates the formula of the envelope L11 as a line passing these data. Similarly, the tonus-information calculating unit 53 extracts time-series data acquired at timing when the heart enters the expansion end period, that is, timing at respective bottoms of the pulsation and creates the formula of the envelope L12 as a line passing these data.

"ΔV" shown in FIG. 5 is obtained by subtracting a value of the envelope L12 at timing when the internal pressure of the compression belt 20 is P from a value of the envelope L11 at the timing. This ΔV can be considered a fluctuation width of the capacity of the compression belt 20 at the time when the internal pressure of the compression belt 20 is P. ΔV described above can also be considered a capacity change of the compression belt 20 under a state in which the internal pressure of the compression belt 20 is adjusted to keep a constant value (P) according to the capacity change of the compression belt 20 involved in a beat of the blood vessel. In other words, ΔV described above can also be considered a capacity change of the compression belt 20 under a state in which pressure applied to the blood vessel wall 100 during the beat of the blood vessel is kept at the constant value (P). Since the fluctuation in the capacity of the compression belt 20 is caused by fluctuation in the capacity on the inner side of the blood vessel wall 100, ΔV can also be considered a fluctuation width of the capacity of the blood vessel wall 100 at the time when the internal pressure of the compression belt 20 is P, that is, "a fluctuation width of the second indicator". The tonus-information calculating unit 53 calculates, for a value of each of internal pressures of the compression belt 20 included in the time-series data, a value of "the fluctuation width of the second indicator" corresponding to the value with the same method as the method explained above.

Figure 6:
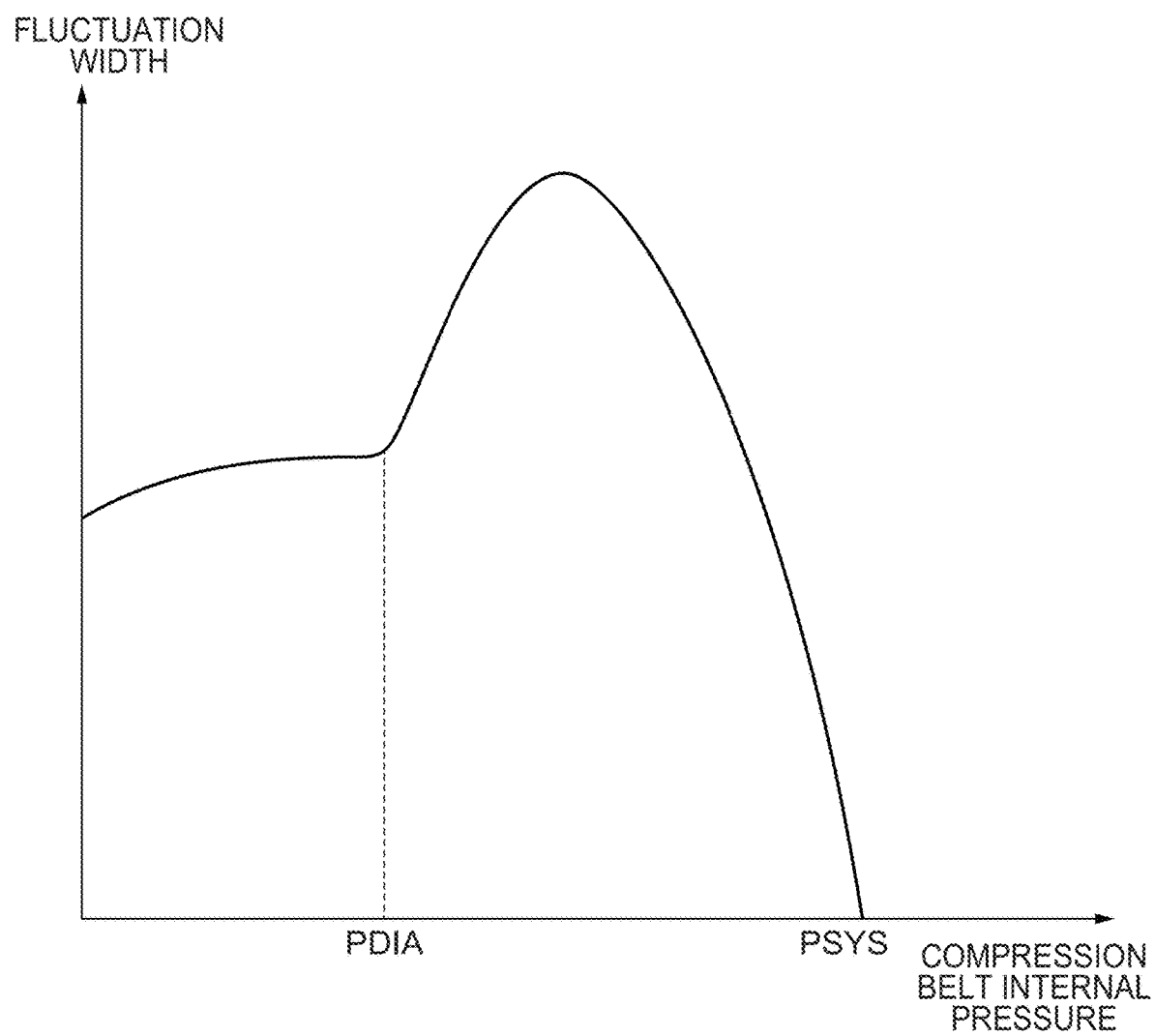
FIG. 6 is a diagram showing an example of a correspondence relation between an internal pressure of a compression belt and a fluctuation width of a second indicator.

A correspondence relation calculated in this way, that is, a correspondence relation between the internal pressure of the compression belt 20 and the fluctuation width of the second indicator should be ideally distributed on a graph shown in FIG. 6. "PDIA" shown in FIG. 6 is a maximum value of the internal pressure of the compression belt 20 for not closing the inner side of the blood vessel wall 100 even when the heart expands and the blood pressure is minimum. The value is referred to as "first pressure PDIA" as well below. "PSYS" in FIG. 6 is a minimum value of the internal pressure of the compression belt 20 for closing the inner side of the blood vessel wall 100 when the heart contracts and the blood pressure is maximum. The value is referred to as "second pressure PSYS" as well below.

When the internal pressure of the compression belt 20 is equal to or smaller than the first pressure PDIA, the inner side of the blood vessel wall 100 is always opened. Accordingly, a gradient of a change in the fluctuation width of the second indicator with respect to a change in the internal pressure of the compression belt 20 is relatively gentle.

When the internal pressure of the compression belt 20 becomes larger than the first pressure PDIA, the inner wall of the blood vessel wall 100 closes every time near timing at the bottom of the pulsation. Accordingly, the gradient of the change in the fluctuation width of the second indicator with respect to the change in the internal pressure of the compression belt 20 suddenly increases.

Thereafter, the gradient described above gradually decreases according to an increase in the internal pressure of the compression belt 20. The fluctuation width of the second indicator changes from an increase to a decrease. Such a change in the fluctuation width of the second indicator involved in the increase in the internal pressure of the compression belt 20 occurs because blood vessel wall elasticity changes according to a difference in involvement of the elastin fibers and the collagen fibers. When the internal pressure of the compression belt 20 further increases, since the force applied to the blood vessel wall 100 increases, the fluctuation width of the second indicator gradually decreases. When the internal pressure of the compression belt 20 reaches the second pressure PSYS, the inner wall of the blood vessel wall 100 is always closed. Therefore, the fluctuation width of the second indicator should ideally be 0 as shown in FIG. 6.

Figure 7:
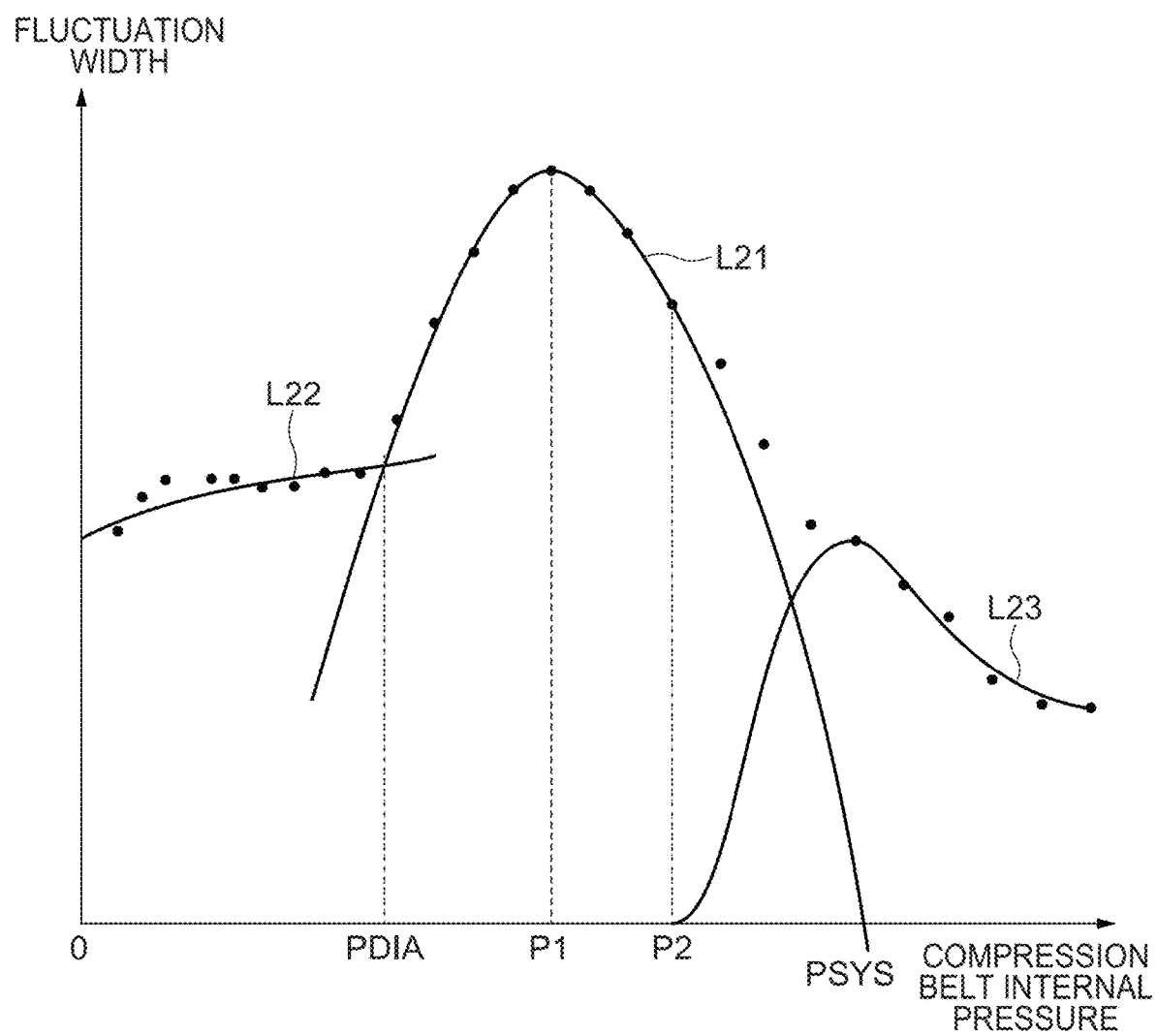
FIG. 7 is a diagram showing an example of the correspondence relation between the internal pressure of the compression belt and the fluctuation width of the second indicator.

A correspondence relation between the internal pressure of the compression belt 20 and the fluctuation width of the second indicator is actually a correspondence relation indicated by respective dots shown in FIG. 7. As shown in FIG. 7, even if the internal pressure of the compression belt 20 reaches the second pressure PSYS, the fluctuation width of the second indicator does not actually decrease to 0. A reason for this is explained with reference to FIG. 8.

Figure 8:
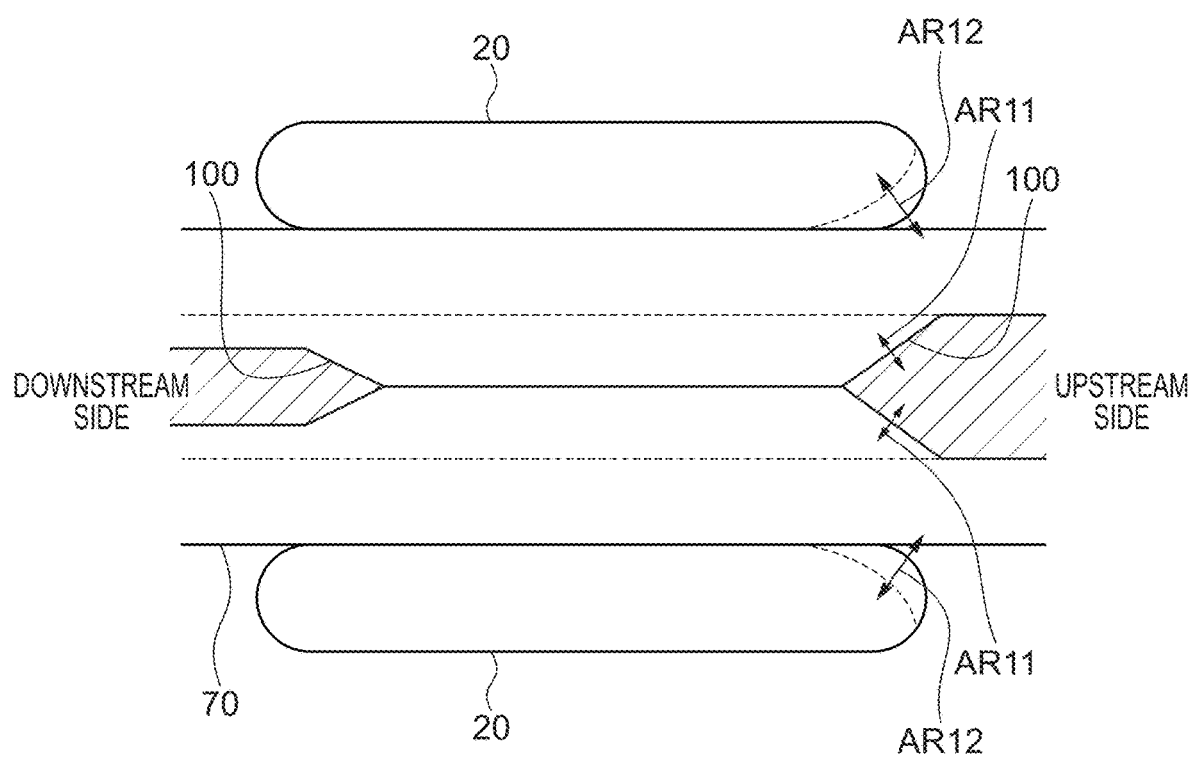
FIG. 8 is a diagram showing a state in which the blood vessel wall is closed by pressure from the compression belt.

In FIG. 8, a cross section of the upper arm 70 around which the compression belt 20 is wound is schematically drawn. In FIG. 8, the internal pressure of the compression belt 20 is larger than the second pressure PSYS and the blood vessel wall 100 is compressed and closed. Accordingly, in a portion shown in FIG. 8, the bloodstream is blocked on the inner side of the blood vessel wall 100.

However, even in a state in which the bloodstream is blocked in this way, the internal pressure of the blood vessel wall 100 is pulsating according to the beat of the heart in a portion further on an upstream side (the right side in FIG. 8) than the compression belt 20 in the blood vessel wall 100. Accordingly, the capacity of the blood vessel wall 100 in this portion pulsates as indicated by an arrow AR11. Since force is applied to the compression belt 20 by the pulsation, the capacity of the compression belt 20 also pulsates as indicated by an arrow AR12. This is a reason why the fluctuation width of the second indicator does not decrease to 0 even if the internal pressure of the compression belt 20 becomes equal to or larger than the second pressure PSYS.

Referring back to FIG. 7, a line L23 shown in FIG. 7 represents an influence of pulsation of an upstream side portion in the blood vessel wall 100 indicated by the arrow AR11 in FIG. 8. The respective dots of the data shown in FIG. 7 are distributed on a graph obtained by superimposing the line L23 in FIG. 7 on the ideal graph shown in FIG. 6. The tonus-information calculating unit 53 calculates each of the first pressure PDIA and the second pressure PSYS based on the data distributed as indicated by the respective dots in FIG. 7.

Specifically, the tonus-information calculating unit 53 approximates, using a quadratic function, data in a portion where the fluctuation width of the second indicator is maximum and the vicinity of the portion among the data shown in FIG. 7. In FIG. 7, a graph of the quadratic function obtained by such approximation is shown as a line L21.

"P1" shown in FIG. 7 is an internal pressure of the compression belt 20 at the time when the fluctuation width of the second indicator is maximum. "P2" shown in FIG. 7 is an internal pressure of the compression belt 20 at the time when the change in the fluctuation width of the second indicator is at an inflection point. This "P2" can also be considered an internal pressure of the compression belt 20 at the time when the influence of the line L23 starts to appear. As the quadratic function indicated by the line L21, it is preferable to adopt a quadratic function that coincides with the data of the fluctuation width at least at two points of P1 and P2 among the data shown in FIG. 7.

The tonus-information calculating unit 53 calculates, as the second pressure PSYS, an internal pressure of the compression belt 20 at the time when a value of the quadratic function obtained by the approximation explained above is 0, the internal pressure being a value larger than P1.

The tonus-information calculating unit 53 approximates, using a quadratic function different from the quadratic function explained above, a plurality of data in a range sufficiently smaller than P1 among the data indicated by the respective dots in FIG. 7. In FIG. 7, a graph of the quadratic function obtained by such approximation is shown as a line L22. The tonus-information calculating unit 53 calculates, as the first pressure PDIA, an internal pressure of the compression belt 20 corresponding to an intersection of the respective quadratic functions obtained by the respective approximations, that is, an intersection in the line L21 and the line L22.

Note that the calculation of the first pressure PDIA and the second pressure PSYS may be performed by a method different from the method explained above. For example, the approximation for calculating the line L21 and the line L22 may be performed using not the quadratic function but another function such as a cubic function or a quartic function. Waveforms of the respective data shown in FIG. 7 may be analyzed to calculate, as the first pressure PDIA, an internal pressure of the compression belt 20 at a point that is an inflection point. In all the aspects, the tonus-information calculating unit 53 is configured to calculate each of the first pressure PDIA and the second pressure PSYS based on a correspondence relation (that is, the respective dots shown in FIG. 7) between the internal pressure of the compression belt 20 and the fluctuation width of the capacity of the compression belt 20.

After calculating each of the first pressure PDIA and the second pressure PSYS, the tonus-information calculating unit 53 calculates a compliance value. The "compliance value" means a gradient of a change in the second indicator corresponding to a change in the internal pressure of the compression belt 20 involved in the beat of the heart.

A method of calculating the compliance value is explained with reference to FIGS. 9A to 9C. In an upper part in each of FIGS. 9A to 9C, a sectional shape of the blood vessel wall 100 at the time when the heart contracts and the blood pressure is the maximum, that is, at the time when the blood pressure in the blood vessel wall 100 is generally equal to the second pressure PSYS is schematically shown. In a lower part in each of FIGS. 9A to 9C, a sectional shape of the blood vessel wall 100 at the time when the heart expands and the blood pressure is the minimum, that is, at the time when the blood pressure in the blood vessel wall 100 is generally equal to the first pressure PDIA is schematically shown.

Figure 9A:
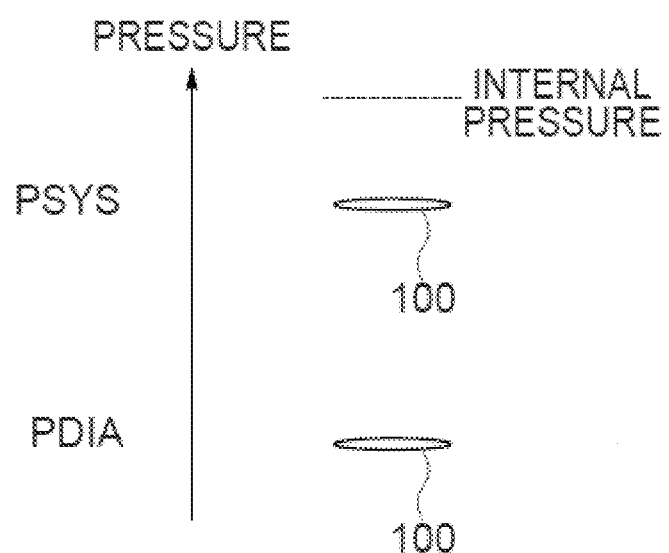
FIGS. 9A to 9C are diagrams showing relations between the internal pressure of the compression belt and states of the blood vessel wall.

In FIG. 9A, a state of the blood vessel wall 100 at the time when the internal pressure of the compression belt 20 is larger than both of the first pressure PDIA and the second pressure PSYS is shown. In this state, the blood vessel wall 100 is always closed by force from the compression belt 20 at both of the time when the heart contracts and the blood pressure is the maximum and the time when the heart expands and the blood pressure is the minimum. When the internal pressure of the compression belt 20 is in such a pressure range, since the capacity of the blood vessel wall 100 does not change, the compliance value, which is an indicator indicating the elastic state of the blood vessel wall 100, cannot be obtained.

Accordingly, the tonus-information calculating unit 53 does not calculate the tonus information for the pressure range.

Figure 9B:
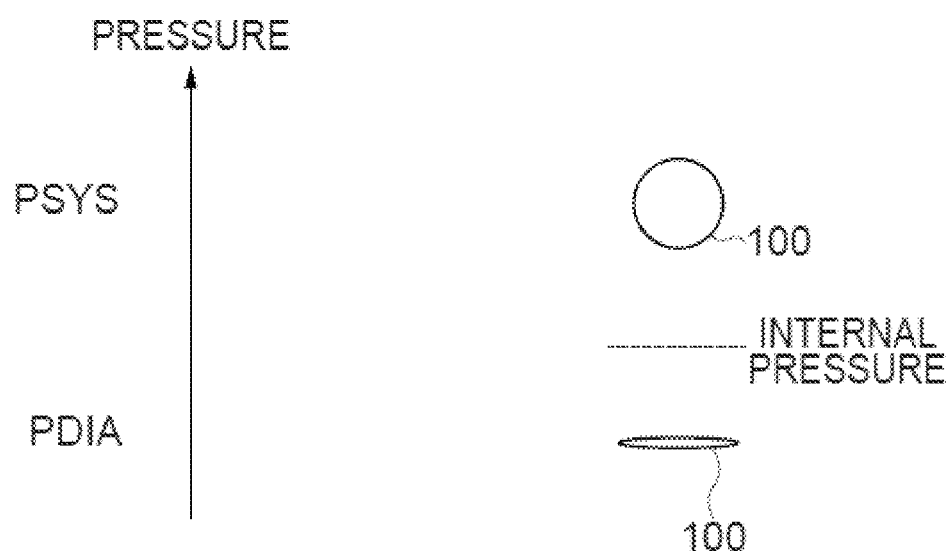

In FIG. 9B, a state of the blood vessel wall 100 at the time when the internal pressure of the compression belt 20 is larger than the first pressure PDIA and is smaller than the second pressure PSYS is shown. In this state, the blood vessel wall 100 is opened when the heart contracts and the blood pressure is the maximum and the blood vessel wall 100 is closed when the heart expands and the blood pressure is the minimum.

When the internal pressure of the compression belt 20 is in this pressure range, a fluctuation width of the internal pressure of the compression belt 20 involved in the beat of the heart is (PSYS−0). Accordingly, when the fluctuation width of the second indicator at respective each internal pressure is represented as "ΔV" and the compliance value is represented as "C", the compliance value for the time when the internal pressure of the compression belt 20 is in this pressure range can be calculated using a formula C=ΔV/PSYS.

Figure 9C:

In FIG. 9C, a state of the blood vessel wall 100 at the time when the internal pressure of the compression belt 20 is smaller than both of the first pressure PDIA and the second pressure PSYS is shown. In this state, the blood vessel wall 100 is always opened at both of the time when the heart contracts and the blood pressure is the maximum and the time when the heart expands and the blood pressure is the minimum.

When the internal pressure of the compression belt 20 is in this pressure range, the fluctuation width of the internal pressure of the compression belt 20 involved in the beat of the heart is (PSYS−PDIA). Accordingly, as in the above explanation, when the fluctuation width of the second indicator at respective each internal pressure is represented as "ΔV" and the compliance value is represented as "C", the compliance value for the time when the internal pressure of the compression belt 20 is in this pressure range can be calculated using a formula C=ΔV/(PSYS−PDIA).

According to the method explained above, the tonus-information calculating unit 53 calculates compliance values corresponding to respective values of the internal pressure of the compression belt 20 for the respective pressure ranges in FIGS. 9A to 9C. Since the compliance value can also be considered a function of the internal pressure P of the compression belt 20, the compliance value can be represented as "C(P)". The respective compliance values can be used as indicators indicating the elastic state of the blood vessel wall 100 that change according to the internal pressure of the compression belt 20.

Subsequently, the tonus-information calculating unit 53 integrates C(P), which is the compliance value, for the internal pressure P of the compression belt 20 up to a predetermined value. As an integration section, for example, a section from the lowest value of the internal pressure P included in the time-series data to the predetermined value only has to be set. When an increase in the internal pressure P in the integration calculation is represented as "ΔP", the integration explained above is calculated by integrating a value of ΔV=C(P)ΔP in a range in which a value of the internal pressure P changes, for example, from 0 to the predetermined value. Any magnitude can be set as the magnitude of the increase ΔP.

A value obtained by the integration is a capacity on the inner side of the blood vessel wall 100 at the time when the internal pressure of the compression belt 20 is the "predetermined value". A combination of the first indicator corresponding to the "predetermined value" explained above and the second indicator corresponding to the "capacity" obtained by the integration is used as an element forming the tonus information. The tonus-information calculating unit 53 performs the integration explained above for "predetermined values" of various values to calculate a plurality of combinations of first indicators and second indicators. It is possible to calculate the tonus information shown in FIG. 3 by plotting the respective combinations of the first indicators and the second indicators on, for example, a two-dimensional graph.

Note that, as the first indicator on the vertical axis of FIG. 3, an indicator different from the indicator in the embodiment can also be used if the indicator is an indicator indicating the pressure applied to the blood vessel wall. For example, a value of the blood pressure may be set as a reference and a value converted to be pressure that is an increase from the reference may be set as the first indicator. The value of the blood pressure in this case only has to be calculated in advance based on the time-series data using, for example, the method described in Japanese Patent No. 6651087.

FIG. 10 is a figure in which a flow of processing executed in order to calculate the tonus information is drawn as a flowchart. In first step Sa1 of the processing, the compression belt 20 is wound around the upper arm 70. Note that internal pressure of the compression belt 20 at this point in time is generally equal to the air pressure.

In step S02 following step S01, processing for raising the internal pressure of the compression belt 20 is performed by the pressure adjusting unit 51. The pressure adjusting unit 51 controls the operations of the air pump 31 and the control valve 32 to raise the internal pressure of the compression belt 20 at predetermined speed. When the pressure sensor 34 detects that the internal pressure of the compression belt 20 has reached a predetermined target pressure, the pressure adjusting unit 51 stops the operation of the air pump 31. As the target pressure, pressure sufficiently higher than an average value of the second pressure PSYS is set. Accordingly, at a point in time when the processing in step S02 is completed, the blood vessel wall 100 is always closed by force from the compression belt 20.

In step S03 following step S02, the pressure adjusting unit 51 starts processing for gradually reducing the internal pressure of the compression belt 20. The pressure adjusting unit 51 controls the operations of the air pump 31 and the control valve 32 to reduce the internal pressure of the compression belt 20 at predetermined speed. This processing is continuously performed until the internal pressure of the compression belt 20 reaches a predetermined stop pressure. As the stop pressure, pressure sufficiently lower than an average value of the first pressure PDIA is set.

When the processing is started in step S03, the processing immediately shifts to step S04 without waiting for the internal pressure of the compression belt 20 to reach the stop pressure. In step S04, the data acquiring unit 52 starts processing for acquiring time-series data. As explained above, the data acquiring unit 52 acquires the time-series data by sampling each of the internal pressure and the capacity of the compression belt 20 at the predetermined cycle. The acquisition of the time-series data is continuously performed until the internal pressure of the compression belt 20 reaches the stop pressure. When the internal pressure of the compression belt 20 reaches the stop pressure, the pressure adjusting unit 51 stops the operation of the air pump 31. The data acquiring unit 52 ends the acquisition of the time-series data. Thereafter, the processing shifts to step S05.

In step S05, the filtering processing by the tonus-information calculating unit 53 is performed. As explained above, the tonus-information calculating unit 53 applies the filtering processing to the time-series data to thereby extract time-series data acquired at the timing when the heart enters the maximum contraction period, that is, the timing at the respective peaks of the pulsation and creates the formula of the envelope L11 shown in FIG. 5 as a line passing these data. Similarly, the tonus-information calculating unit 53 extracts time-series data acquired at the timing when the heart enters the expansion end period, that is, the timing at the respective bottoms of the pulsation and creates the formula of the envelope L12 shown in FIG. 5 as a line passing these data.

In step S06 following step S05, as explained with reference to FIG. 5, the tonus-information calculating unit 53 performs processing for calculating a value ($\Delta V$ in FIG. 5) of a fluctuation width of the second indicator corresponding to each of the internal pressures of the compression belt 20 included in the time-series data. Consequently, the data indicated by the respective dots shown in FIG. 7 is acquired as a correspondence relation between the internal pressure of the compression belt 20 and a fluctuation width of the second indicator corresponding to the internal pressure.

In step S07 following step S06, the tonus-information calculating unit 53 performs processing for calculating a value of each of the first pressure PDIA and the second pressure PSYS. A method of calculating the value is as explained above with reference to FIG. 7 and the like.

In step S08 following step S07, the tonus-information calculating unit 53 performs processing for calculating the compliance value. The compliance value is calculated for a value of each of the internal pressures of the compression belt 20 included in the time-series data. As explained above with reference to FIG. 9, the tonus-information calculating unit 53 calculates, for respective data at the time when the internal pressure of the compression belt 20 is larger than the first pressure PDIA and is smaller than the second pressure PSYS, compliance values corresponding to the respective internal pressures using the formula $C=\Delta V/PSYS$. The tonus-information calculating unit 53 calculates, for respective data at the time when the internal pressure of the compression belt 20 is smaller than both of the first pressure PDIA and the second pressure PSYS, compliance values corresponding to the respective internal pressures using the formula $C=\Delta V/(PSYS-PDIA)$. The compliance value is calculated as a function C(P) of the internal pressure P of the compression belt 20 by the processing in step S08.

In step S09 following step S08, the tonus-information calculating unit 53 performs processing for integrating, for the internal pressure P of the compression belt 20, the compliance value calculated as the function C(P) of the internal pressure P up to a predetermined value. As explained above, the processing is performed for various "predetermined values". Consequently, a combination of first indicators corresponding to the respective "predetermined values" and a second indicator corresponding to a value (a capacity on the inner side of the blood vessel wall 100) obtained by the integration explained above is calculated as the tonus information.

In step S10 following step S09, the output unit 54 performs processing for outputting the tonus information calculated in step S09 to the outside. As explained above, the output tonus information is drawn on the screen of the display device 60 as the same two-dimensional graph as the two-dimensional graph shown in FIG. 3. Consequently, the tonus information is presented to the user of the biological information measuring apparatus 10.

As explained above, in the biological information measuring apparatus 10 according to this embodiment, the tonus information indicating the correspondence relation between the first indicator indicating the pressure applied to the blood vessel wall 100 of the living body and the second indicator indicating the capacity on the inner side of the blood vessel wall 100 is calculated based on the time-series data. As components for acquiring the time-series data, the ultrasonic imaging device, the strain gauge, and the like of the related art are unnecessary. A relatively simple and small component like a general manometer for home use can be adopted. Therefore, according to this embodiment, it is possible to measure the tonus information of the blood vessel, although the simple and small component is adopted.

The tonus information calculated by the tonus-information calculating unit 53 in this embodiment can be represented as the two-dimensional graph as shown in FIG. 3. Therefore, the tonus information includes the value of the second indicator corresponding to each of the values of the plurality of first indicators. Since the biological information measuring apparatus 10 calculates and outputs the tonus information of such a form, it is possible to provide various kinds of information corresponding to purposes to the user, for example, quantize a state of the blood vessel wall 100 using the blood vessel modulus of elasticity represented by the formula of "V(dP/dV)" explained above or quantize the state of the blood vessel wall 100 as ($\Delta V/V$) using the change amount $\Delta V$ of the second indicator at the time when the blood vessel wall 100 is relaxed and the value (V) of the second indicator before the relaxation.

The tonus-information calculating unit 53 in this embodiment is configured to calculate, as a fluctuation width of the second indicator, a fluctuation width of the capacity of the compression belt 20 that fluctuates according to the beat of the heart and calculate the tonus information using the fluctuation width. The fluctuation width of the second indicator, that is, the fluctuation width of the indicator indicating the capacity of the blood vessel wall 100 can be calculated based on the capacity of the compression belt 20. Therefore, it is unnecessary to use a complicated device such as the ultrasonic imaging device of the related art.

The tonus-information calculating unit 53 integrates the compliance value C(P) for the internal pressure P of the compression belt 20 up to a predetermined value to calculate a value of the second indicator corresponding to the predetermined value. The second indicator indicating the capacity on the inner side of the blood vessel wall 100 can be calculated by not using the ultrasonic imaging device, the strain gauge, and the like but simply integrating the compliance value C(P) obtained by the time-series data. Therefore, it is possible to form the biological information measuring apparatus 10 in a simple and small configuration.

The tonus-information calculating unit 53 calculates each of the first pressure PDIA and the second pressure PSYS with the method explained above based on the correspondence relation between the internal pressure of the compression belt 20 and the fluctuation width of the capacity of the compression belt 20, that is, the correspondence relation indicated by the respective dots shown in FIG. 7. Consequently, it is possible to accurately calculate each of the first pressure PDIA and the second pressure PSYS and use the first pressure PDIA and the second pressure PSYS for calculation of the compliance value.

The tonus-information calculating unit 53 calculates each of the first pressure PDIA and the second pressure PSYS in advance as explained above and, then, in a range in which the internal pressure of the compression belt 20 is smaller than the first pressure PDIA, calculates the compliance value by dividing the fluctuation width of the second indicator by a value obtained by subtracting the first pressure PDIA from the second pressure PSYS. That is, the tonus-information calculating unit 53 calculates the compliance value using the formula of $C=\Delta V/(PSYS-PDIA)$ as explained above.

In a range in which the internal pressure of the compression belt 20 is larger than the first pressure PDIA and smaller than the second pressure PSYS, the tonus-information calculating unit 53 calculates the compliance value by dividing the fluctuation width of the second indicator by a value of the second pressure PSYS. That is, the tonus-information calculating unit 53 calculates the compliance value using the formula of $C=\Delta V/PSYS$ as explained above.

As explained above, the tonus-information calculating unit 53 in this embodiment calculates, for the internal pressure of the compression belt 20, the compliance value using an appropriate formula corresponding to each of a pressure range shown in FIG. 9B and a pressure range shown in FIG. 9C. Consequently, it is possible to accurately calculate each of the compliance value and the tonus information based on the compliance value.

The biological information measuring apparatus 10 further includes the output unit 54 for outputting the tonus information. Consequently, it is possible to present the calculated tonus information to the user in various forms.

This embodiment is explained above with reference to the specific examples. However, the present disclosure is not limited to these specific examples. These specific examples subjected to design changes by those skilled in the art as appropriate are included in the scope of the present disclosure as long as the specific examples include the characteristics of the present disclosure. The respective elements included in the respective specific examples explained above and the dispositions, the conditions, the shapes, and the like of the elements are not limited to the illustrated ones and can be changed as appropriate. The combinations of the respective elements included in the respective specific examples explained above can be changed as appropriate as long as a technical contradiction does not occur.

The control device and the control method described in the present disclosure may be realized by one or a plurality of dedicated computers provided by configuring a processor programed to execute one or a plurality of functions embodied by a computer program and a memory. The control device and the control method described in the present disclosure may be realized by a dedicated computer provided by configuring a processor including one or a plurality of dedicated hardware logic circuits. The control device and the control method described in the present disclosure may be realized by one or a plurality of dedicated computers configured by a combination of a processor programmed to execute one or a plurality of functions and a memory and a processor including one or a plurality of hardware logic circuits. The computer program may be stored in a computer-readable non-transitory tangible recording medium as an instruction to be executed by a computer. The dedicated hardware logic circuit and the hardware logic circuit may be realized by a digital circuit including a plurality of logic circuits or an analog circuit.

What is claimed is:

1. A biological information measuring apparatus comprising:
   a compression belt to be wound around a part of a living body;
   an air pump configured to blow out air toward the compression belt;
   a control valve configured to adjust an amount of the air blown into the compression belt and to adjust an amount of the air discharged from the compression belt;
   a pressure sensor configured to measure an internal pressure of the compression belt;
   a flow sensor configured to measure each of a flow rate of the air supplied to the compression belt and a flow rate of the air discharged from the compression belt;
   a pressure adjusting unit configured to control the operations of the air pump and the control valve respectively to change the internal pressure of the compression belt;
   a data acquiring unit configured to acquire correlation data indicating corresponding relation between the internal pressure of the compression belt and a capacity of the compression belt in a period in which the internal pressure of the compression belt is changing; and
   a tonus-information calculating unit configured to calculate, based on the correlation data including the correspondence relation between the internal pressure of the compression belt and the capacity of the compression belt, tonus information indicating a correspondence relation between a first indicator indicating pressure applied to a blood vessel wall of the living body and a second indicator indicating a capacity of an inner side of the blood vessel wall, wherein
   the pressure adjusting unit controls the operations of the air pump and the control valve to raise the internal pressure of the compression belt, and stops the operation of the air pump when the pressure sensor detects that the internal pressure of the compression belt has reached a predetermined target pressure, and controls the operations of the air pump and the control valve to reduce the internal pressure of the compression belt, and stops the operation of the air pump when the internal pressure of the compression belt reaches a predetermined stop pressure,
   the data acquiring unit acquires the time-series data indicating a change of the internal pressure of the compression belt by sampling the internal pressure of the compression belt at a predetermined cycle by the pressure sensor for a period from the time when the pressure adjusting unit starts the control to reduce the internal pressure of the compression belt until the time when the pressure adjusting unit stops the operation of the air pump,
   the data acquiring unit acquires the time-series data indicating a change of the capacity of the compression belt by sampling the flow rate of the air discharged from the compression belt at the predetermined cycle by the flow sensor for the period, and calculating the capacity of the compression belt using the flow rate of the air discharged from the compression belt sampled at the predetermined cycle,
   the data acquiring unit acquires the correlation data indicating the correspondence relation between the internal pressure of the compression belt and the capacity of the compression belt based on the time-series data indicating a change of the internal pressure of the compression belt and the time-series data indicating a change of the capacity of the compression belt, the tonus-information calculating unit creates a first formula and a second formula based on the correlation data indicating a correspondence relation between the internal pressure of the compression belt and the capacity of the compression belt, the first formula being a formula of an envelope passing the correlation data acquired at timing at respective peaks of a pulsation in the correlation data, the second formula being a formula of an envelope passing the correlation data acquired at timing at respective bottoms of the pulsation in the correlation data, the tonus-information calculating unit calculates the fluctuation width of the second indicator corresponding to each of the internal pressures by subtracting a value obtained by the second formula from a value obtained by the first formula, the tonus-information calculating unit calculates a correspondence relation between the internal pressure of the compression belt and the fluctuation width of the second indicator, the tonus-information calculating unit approximates, using a first function, data in a portion, where the fluctuation width of the second indicator is maximum, and the vicinity of the portion among data indicating the correspondence relation between the internal pressure of the compression belt and the fluctuation width of the second indicator, the tonus-information calculating unit approximates, using a second function, a plurality of data in a range smaller than the data in the portion and the vicinity of the portion among the data indicating the correspondence relation between the internal pressure of the compression belt and the fluctuation width of the second indicator, the tonus-information calculating unit calculates, as a first pressure, an internal pressure of the compression belt corresponding to an intersection of the first function and the second function, the tonus-information calculating unit calculates, as a second pressure, an internal pressure of the compression belt at the time when a value of the first function is 0, the tonus-information calculating unit calculates a compliance value, which is a gradient of a change of the second indicator corresponding to the change in the internal pressure of the compression belt, by dividing the fluctuation width of the second indicator by a value of the second pressure in a range in which the internal pressure of the compression belt is larger than the first pressure and the internal pressure of the compression belt is smaller than the second pressure, the tonus-information calculating unit calculates the compliance value by dividing the fluctuation width of the second indicator by a value obtained by subtracting the first pressure from the second pressure in a range in which the internal pressure of the compression belt is smaller than the first pressure and the internal pressure of the compression belt is smaller than the second pressure, the tonus-information calculating unit integrates the compliance value up to a predetermined value to calculate a value of the second indicator corresponding to the predetermined value, and the tonus-information calculating unit calculates a correspondence relation between the first indicator and the second indicator, which is obtained by integrating the compliance value, as the tonus-information.

2. The biological information measuring apparatus according to claim 1, wherein a value of the second indicator corresponding to each of values of a plurality of the first indicators is included in the tonus information calculated by the tonus-information calculating unit.

3. The biological information measuring apparatus according to claim 1, wherein the tonus-information calculating unit calculates each of the first pressure and the second pressure based on a correspondence relation between the internal pressure of the compression belt and the fluctuation width of the capacity of the compression belt.

4. The biological information measuring apparatus according to claim 1, further comprising an output unit configured to output the tonus information.

* * * * *